United States Patent
Andersson et al.

(10) Patent No.: US 6,812,456 B2
(45) Date of Patent: *Nov. 2, 2004

(54) MICROFLUIDIC SYSTEM (EDI)

(75) Inventors: Per Andersson, Uppsala (SE); Magnus Gustafsson, Solna (SE); Anders Palm, Uppsala (SE); Susanne Wallenborg, Uppsala (SE); Cecilia Hellermark, Lidingo (SE)

(73) Assignee: Gyros AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/148,083
(22) PCT Filed: Mar. 19, 2002
(86) PCT No.: PCT/SE02/00538
§ 371 (c)(1), (2), (4) Date: May 24, 2002
(87) PCT Pub. No.: WO02/075775
PCT Pub. Date: Sep. 26, 2002

(65) Prior Publication Data
US 2003/0066957 A1 Apr. 10, 2003

Related U.S. Application Data

(63) Continuation-in-part of application No. 09/812,123, filed on Mar. 19, 2001, now Pat. No. 6,717,136.
(60) Provisional application No. 60/315,471, filed on Aug. 28, 2001.

(30) Foreign Application Priority Data

Mar. 19, 2001 (SE) .............................................. 0100951
Jan. 28, 2002 (SE) .............................................. 0200242

(51) Int. Cl.[7] .............................................. H01J 49/00
(52) U.S. Cl. ..................................................... 250/288
(58) Field of Search ................................. 250/281–300

(56) References Cited

U.S. PATENT DOCUMENTS

| 3,852,595 A | * 12/1974 | Aberth ........................ 250/288 |
| 4,465,935 A | 8/1984 | von Criegern et al. |
| 5,115,131 A | 5/1992 | Jorgenson et al. |
| 5,197,185 A | 3/1993 | McCoy et al. |

(List continued on next page.)

FOREIGN PATENT DOCUMENTS

| EP | 0 073 513 A1 | 8/1982 |
| EP | 0 073 513 B1 | 8/1982 |
| EP | 0 073 513 B2 | 8/1982 |
| EP | 0 655 618 A2 | 5/1995 |
| WO | WO/97/04297 | 2/1997 |
| WO | WO 97/21090 | 6/1997 |

(List continued on next page.)

OTHER PUBLICATIONS

Zhang, B. et al. Microfabricated Devices for Capillary Electrophoresis–Electrospray Mass Spectrometry; Analytical Chemistry, vol. 71, No. 15, Aug. 1, 1999 pp 3258–3264.
Kido, H. et al, Disc–based Immunoassay Microarrays; Analytica Chimica Acta 411 (2000).

Primary Examiner—Nikita Wells
Assistant Examiner—Christopher M. Kalivoda
(74) Attorney, Agent, or Firm—Fulbright & Jaworski LLP

(57) ABSTRACT

A microfluidic device in form of a disc comprising an MS-port for presentation of an MS-analyte to an EDI-MS apparatus, said MS-port is a part of a microchannel structure (I) comprising an inlet port for a sample, and comprises an EDI-area having a conductive layer (I) and an EDI-surface from which the MS-analyte is to be desorbed/ionised. The device is characterized in that layer (I) has a conductive connection and/or that there is a calibrator area in the proximity of each of said one, two or more MS-ports. In a typical variant the MS-port is in the form of a depression that is in fluid communication with upstream part of microchannel structure (I).

20 Claims, 8 Drawing Sheets

U.S. PATENT DOCUMENTS

Figure 1:
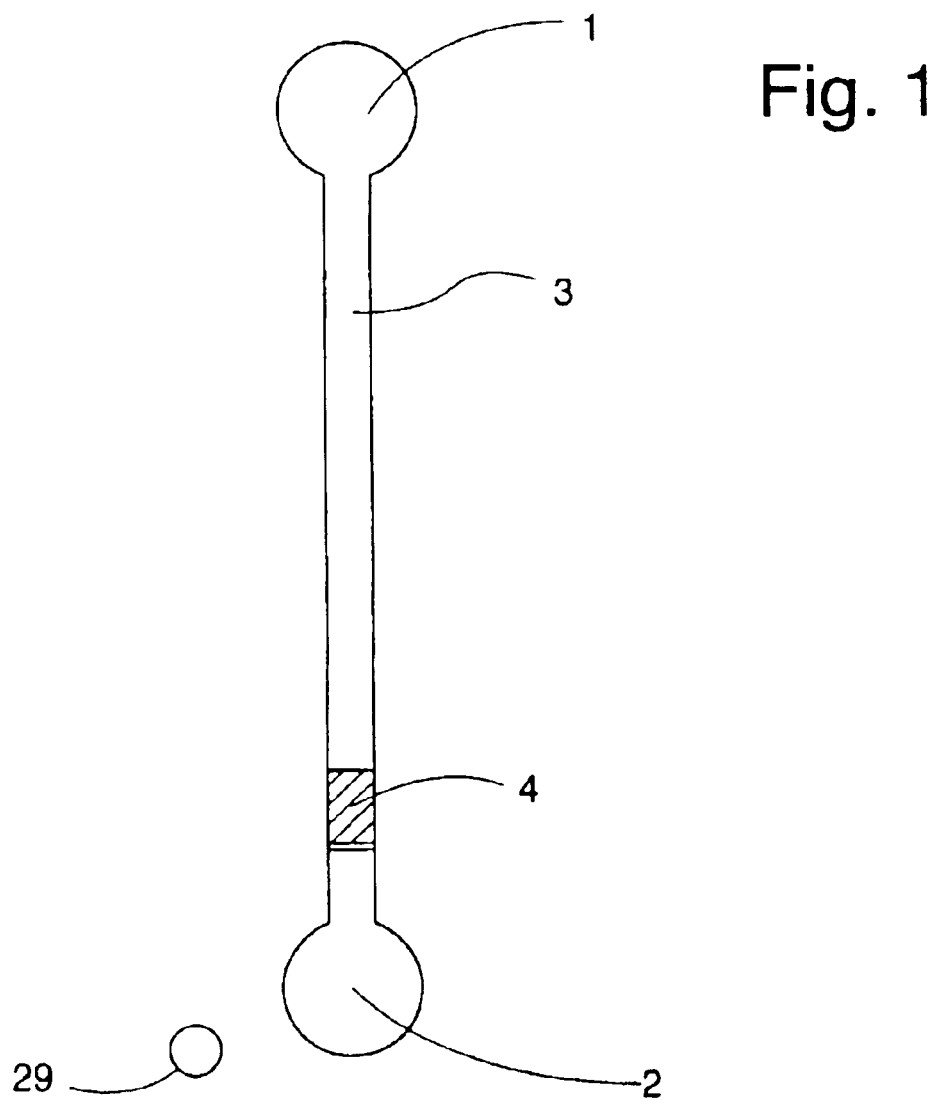

| | | | |
|---|---|---|---|
| 5,310,523 A | | 5/1994 | Smethers et al. |
| 5,608,519 A | * | 3/1997 | Gourley et al. ............. 356/318 |
| 5,637,469 A | | 6/1997 | Wilding et al. |
| 5,705,813 A | | 1/1998 | Apffel et al. |
| 5,716,825 A | | 2/1998 | Hancock et al. |
| 5,866,345 A | | 2/1999 | Wilding et al. |
| 5,872,010 A | | 2/1999 | Karger et al. |
| 5,969,353 A | | 10/1999 | Hsieh |
| 6,063,589 A | | 5/2000 | Kellogg et al. |
| 6,110,343 A | | 8/2000 | Ramsey et al. |
| 6,143,247 A | | 11/2000 | Sheppard, Jr. et al. |
| 6,302,134 B1 | | 10/2001 | Kellogg et al. |
| 6,319,468 B1 | | 11/2001 | Sheppard, Jr. et al. |
| 6,319,469 B1 | | 11/2001 | Mian et al. |
| 6,326,083 B1 | | 12/2001 | Yang et al. |
| 2002/0076354 A1 | * | 6/2002 | Cohen .......................... 422/72 |
| 2002/0118355 A1 | * | 8/2002 | Worthington et al. ......... 356/72 |
| 2003/0066959 A1 | * | 4/2003 | Andersson et al. ......... 250/288 |

FOREIGN PATENT DOCUMENTS

| | | |
|---|---|---|
| WO | 00/30167 A1 | 5/2000 |
| WO | WO 00/50172 | 8/2000 |
| WO | 00/67293 A1 | 11/2000 |
| WO | WO 01/47637 A1 | 7/2001 |
| WO | WO/01/54810 A1 | 8/2001 |
| WO | WO 01/63241 A2 | 8/2001 |

* cited by examiner

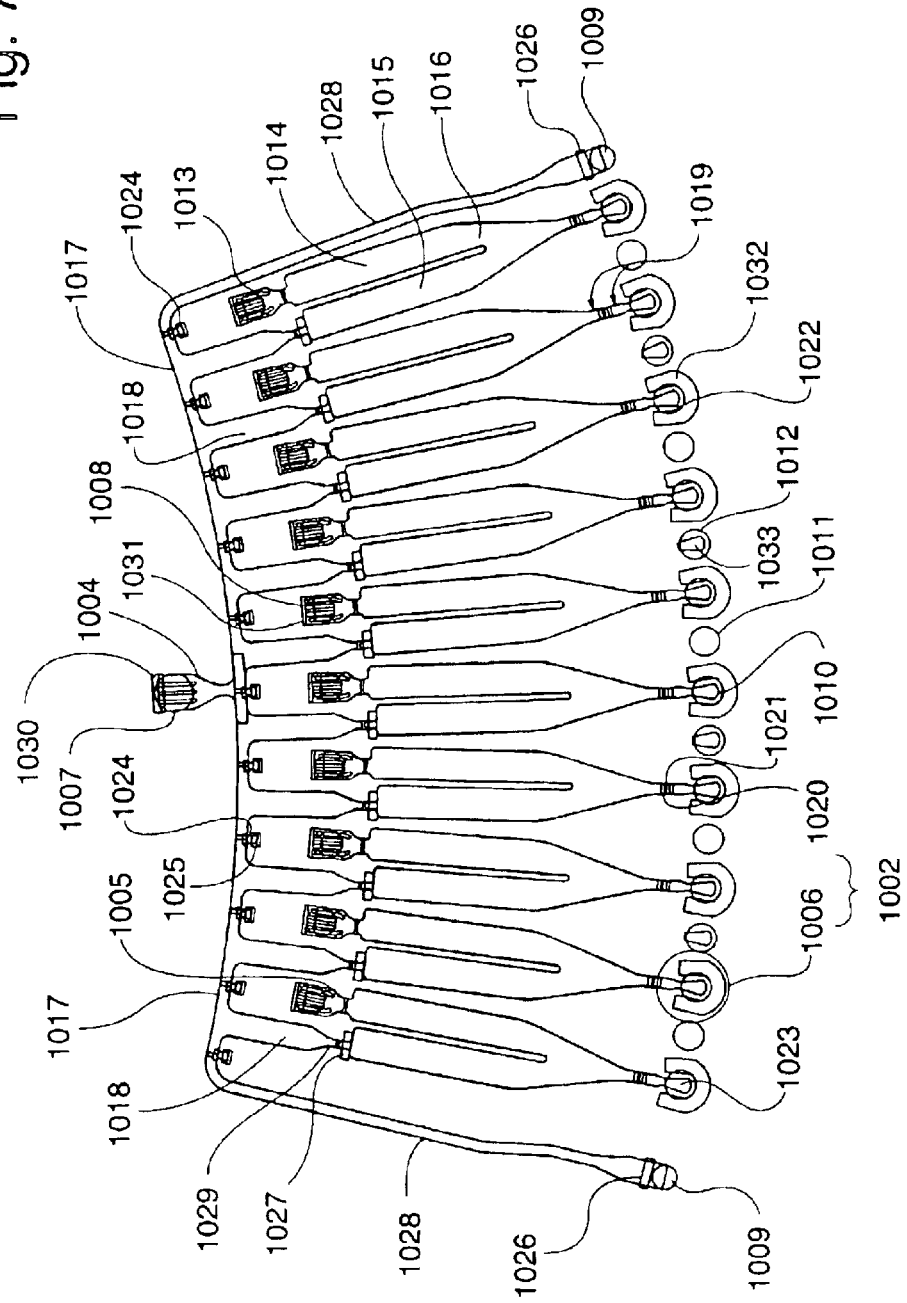

MICROFLUIDIC SYSTEM (EDI)

This application is a National Stage Application of International application Ser. No. PCT/SE02/00538 filed Mar. 19, 2002 which is a continuation-in-part of U.S. Application No. 09/812,123 filed Mar. 19, 2001 and Swedish Application No. SE0100951-3 filed Mar. 19, 2001; and claims priority to U.S. Provisional Application No. 60/315,471 filed Aug. 28, 2001 and Swedish Application No. SE0200242-6 filed Jan. 28, 2002.

TECHNICAL FIELD

The present invention relates to a microfluidic device, which can be interfaced to a mass spectrometer (MS). The device comprises a microchannel structure, which has a first port (inlet port) and a second port (outlet port). A sample to be analysed is applied to the first port and presented to the mass spectrometer in the second port. This second port will be called an MS-port. There may be additional inlet and outlet ports, and also additional identical or similar microchannel structures. During passage through the microchannel structure the sample is prepared to make it suitable for analysis by mass spectrometry.

The sample presented in an MS-port will be called an MS-sample. An analyte in an MS-sample is an MS-analyte. "Sample" and "analyte" without prefix will primarily refer to a sample applied to an inlet port.

Conductive and non-conductive properties are with respect to conducting electricity.

The present invention concerns mass spectrometry in which the MS-samples are subjected to Energy Desorption/Ionisation from a surface by input of energy (EDI MS). Generically this kind of process will be called EDI and the surface an EDI-surface in the context of the invention. Typically EDIs are thermal desorption/ionisation (TDI), plasma desorption/ionisation (PDI) and various kinds of irradiation desorption/ionisation (IDI) such as by fast atom bombardment (FAB), electron impact etc. In the case a laser is used the principle is called laser desorption/ionisation (LDI). Desorption may be assisted by presenting the MS analyte together with various helper substances or functional groups on the surface. Common names are matrix assisted laser desorption/ionisation (MALDI) including surface-enhanced laser desorption/ionisation (SELDI). For MALDI see the publications discussed under Background Publications below. For SELDI see WO 0067293 (Ciphergen Biosystems).

The term "EDI-area" comprises the EDI-surface as such and the part of a substrate covered by this surface, e.g. the part of the substrate that is under the EDI-surface. Compare the description of FIG. 4.

The term "microformat" means that in at least a part of a microchannel structure the depth and/or width is in the microformat range, i.e. $<10^3$ μm, preferably $<10^2$ μm. The depth and/or width are within these ranges essentially everywhere between an inlet port and an outlet port, e.g. between a sample inlet port and an MS-port. The term "microchannel structures" includes that the channels are enclosed in a substrate.

The term "microfluidic device" means that transport of liquids and various reagents including analytes are transported between different parts within the microchannel structures by a liquid flow.

BACKGROUND PUBLICATIONS.

For some time there has been a demand for microfluidic sample handling and preparation devices with integrated MS-ports. This kind of devices would facilitate automation and parallel experiments, reduce loss of analyte, increase reproducility and speed etc.

WO 9704297 (Karger et al) describes a microfluidic device that has an outlet port that is claimed useful when conducting electrospray ionisation mass spectrometry (ESI MS), atmospheric pressure chemical ionisation mass spectrometry (APCI MS), matrix assisted laser desorption/ionisation mass spectrometry (MALDI MS) and a number of other analytical principles.

U.S. Pat. No. 5,705,813 (Apffel et al) and U.S. Pat. No. 5,716,825 (Hancock et al) describe a microfluidic chip containing an MS-port. After processing a sample within the chip the sample will appear in the MS-port. The whole chip is then placed in an MALDI-TOF MS apparatus. The microfluidic device comprises (a) an open ionisation surface that may be used as the probe surface in the vaccum gate of an MALDI-TOF MS apparatus (column 6, lines 53–58 of U.S. Pat. No. 5,705,813), or (b) a pure capture/reaction surface from which the MS-analyte can be transferred to a proper probe surface for MALDI-TOF MS (column 12, lines 13–34, of U.S. Pat. No. 5,716,825).

These publications suggest that means for transporting the liquid within a microchannel structure of the device are integrated with or connected to the device. These means are electrical connections, pumps etc, which impose an extra complexity on the design and use and may negatively influence the production costs, easiness of handling etc.

Although both U.S. Pat. No. 5,705,813 (Apffel et al) and U.S. Pat. No. 5,716,825 (Hancock et al) explicitly concern microfluidic devices, they are scarce about the proper fluidics around the MALDI ionisation surface, the proper crystallisation on the MALDI ionisation surface, the proper geometry of the port in relation to crystallisation, evaporation, the incident laser beam etc, the conductive connections to the MALDI ionisation surface for MALDI MS analysis.

These features are important in order to manage with interfacing a microfluidic device to an MALDI mass spectrometer.

WO 9704297 (Karger et al) and WO 0247913 (Gyros A B) suggest a radial or spoke arrangement of the microchannel structures of a microfluidic device.

WO 9721090 (Mian et al) (page 30, lines 3–4, and page 51, line 10) and WO 0050172 (Burd Mehta) (page 55, line 14) suggest in general terms that their microfluidic systems might be used for preparing samples that are to be analysed by mass spectrometry. WO 9721090 is explicitly related to a system in which centrifugal force is used for driving the liquid flow.

A number of publications referring to the use of centrifugal force for moving liquids within microfluidic systems have appeared during the last years. See for instance WO 9721090 (Gamera Bioscience), WO 9807019 (Gamera Bioscience) WO 9853311 (Gamera Bioscience), WO 9955827 (Gyros A B), WO 9958245 (Gyros A B), WO 0025921 (Gyros A B), WO 0040750 (Gyros A B), WO 0056808 (Gyros A B), WO 0062042 (Gyros A B), WO 0102737 (Gyros A B), WO 0147637, (Gyros A B), WO 0154810 (Gyros A B), WO 0147638 (Gyros A B), WO 0146465 (Gyros A B).

U.S. Ser. No. 60/315,471 and the corresponding International Patent Application WO 02074438 discuss various designs of microfluidic functions, some of which can be applied to the present invention.

Kido et al., ("Disc-based immunoassay microarrays", Anal. Chim. Acta 411 (2000) 1–11) has described microspot immunoassays on a compact disc (CD). The authors suggest that a CD could be used as a continuous sample collector for microbore HPLC and subsequent detection for instance by MALDI MS. In a preliminary experiment a piece of a CD manufactured in polycarbonate was covered with gold and spotted with a mixture of peptides and MALDI matrix.

OBJECTS OF THE INVENTION.

A first object is to provide improved means and methods for transporting samples, analytes including fragments and derivatives, reagents etc in microfluidic devices that are capable of being interfaced with a mass spectrometer that require energy desorption/ionisation of an MS-analyte from a surface by input of energy.

A second object is to provide improved microfluidic methods and means for sample handling before presentation of a sample analyte as an MS-analyte. Sub-objects are to provide an efficient concentration, purification and/or transformation of a sample within the microfluidic device while maintaining a reproducible yield/recovery, and/or minimal loss of precious material.

A third object is to provide improved microfluidic methods and means that will enable efficient and improved presentation of an MS-sample/MS-analyte. This object applies to MS-samples that are presented on an EDI-surface.

A fourth object is to enable reproducible mass values from an MS-sample that is presented on an EDI surface that is present in a microfluidic device A fifth object is to provide improved microfluidic means and methods for parallel sample treatment before presentation of the MS-analyte from an EDI-surface to mass spectrometry. The improvements of this object refer to features such as accuracy in concentrating, in chemical transformation, in required time for individual steps and for the total treatment protocol etc. By parallel sample treatment is meant that two or more sample treatments are run in parallel in different microchannel structures within the same microfluidic device. The number of parallel runs may be more than five, such as more than 10, 50, 80, 100, 200, 300 or 400 runs. Particular important numbers of parallel samples are below or equal to the standard number of wells in microtiter plates, e.g. 96 or less, 384 or less, 1536 or less, etc A sixth object is to provide a cheap and disposable microfluidic device unit enabling parallel sample treatments and having one or more MS-ports that are adapted to a mass spectrometer that require energy desorption/ionisation of an MS-analyte from a surface by input of energy.

SUMMARY OF THE INVENTION.

The present inventors have recognized that the optimisation of an EDI-area in a microfluidic device is related to
  (a) the design and/or positioning of a conductive layer in the EDI-area, and/or
  (b) the need of a calibrator area associated with an EDI MS-port, and/or
  (c) the need of a proper conductive connection to the EDI-area for MS analysis.

The conductive connection will support the proper voltage and/or charge transport at the EDI-area, for instance. Improper conductive properties may negatively affect the mass accuracy, sensitivity, resolution etc. The importance of (a)–(c) increases if there is a plurality of microchannel structures in the microfluidic device.

The present inventors have also recognized that several of the above-mentioned objects can be met in the case inertia force is used for transportation of a liquid within a microfluidic device as defined in this specification. This is applicable to liquid, such as washing liquids and liquids containing at least one of (a) the analyte including derivatives and fragments thereof, (b) a reagent used in the transformation of the sample/analyte, etc.

DETAILED DESCRIPTION OF THE INVENTION

The first aspect of the invention is a microfluidic device in form of a disc comprising an MS-port for presentation of an MS-analyte to an EDI-MS apparatus. The MS-port is a part of a microchannel structure (I) which comprises an inlet port for a sample. The MS-port also comprises an EDI-area with a conductive layer (I) and an EDI-surface from which the MS-analyte is to be desorbed/ionised. The disc is characterized in that layer (I) has a conductive connection and/or that there is a calibrator area in the proximity of said MS-port.

The MS-port typically is in the form of a wall or depression with an opening to ambient atmosphere and in fluid communication microchannel structure (I). As discussed in more detail below the disc may comprise two or more of microchannel structure (I), i.e. a plurality of them. Layer (I) may be placed at different positions in the EDI-area.

A second aspect of the invention is a method for transforming a liquid sample containing an analyte to an MS-sample containing an MS-analyte and presenting the MS-sample to a mass spectrometer. The method is characterized in comprising the steps of:
  (a) providing a microfluidic device as defined in this specification,
  (b) applying the liquid sample to an inlet port of one or more of the covered microchannel structures of the microfluidic device,
  (c) transforming the liquid sample to an MS-sample containing the MS-analyte within at least one the microchannel structures to which a sample has been applied in step (b), and
  (d) presenting the MS-analyte to the mass spectrometer.

A variant of the second aspect is a method for collecting mass spectrometric data of an analyte or an analyte-derived entity, for instance in order to gain molecular weight and structure information about an analyte. The analyte-derived entity is then formed in the innovative microfluidic device according to steps (a)–(d) in the preceding paragraph.

The various innovative embodiments of the invention are further defined in the text below including the claims.

Liquid Transport

The liquid flow used for transport of reagents, analyte, analyte derived entities etc within the microchannel structures may be driven by electrokinetic forces and/or by non-electrokinetic forces. Typical non-electrokinetic forces are inertia force, such as centrifugal force, capillary forces, forces created by pressure differences etc. The term "forces created by pressure differences" includes hydrostatic pressure created within certain kinds of microchannel structures by the combined action of spinning and application of a series of liquid aliquots (see below and WO 0146465 (Gyros A B)).

In preferred variants, the liquid flow within the individual microchannel structures of a device is created by the application of inertia force. Inertia force may be the driving force in only a part of a microchannel structure or the whole way from an inlet port to an MS-port and/or to any other outlet port. It is believed that the most general and significant advantages of using inertia force will be accomplished in so called transporting zones, i.e. between zones having predetermined functionalities, or for overcoming or passing through valve functions within a microchannel structure (capillary junctions, hydrophobic breaks etc). See below.

At the priority date the most important inertia force to be used in the innovative devices is centrifugal force, i.e. spinning of the device in order to accomplish an outward radial transportation of liquid which is present in a microchannel structure that comprise parts at different radial distances from the spinning axis (axis of symmetry). The spinning axis is perpendicular to the plane of the disc. The disc/device is preferably circular and centrifugal force is used in at least a part of each microchannel structures, for instance to take the sample into an MS-port.

Inertia force, such as centrifugal force, may be combined with one or more other kinds of driving forces. The combination may be in the same part of a microchannel structure. The combination may also mean that inertia force is utilized for transport in a part where the flow shall be directed outwards towards the periphery of a circular disc and other forces in some other part for creating a flow inwards or more or less parallel to the periphery of a disc. Capillary force may typically be used to transport a liquid aliquot from an inlet port into a microchannel associated with the inlet port. This kind of microchannels may be directed inwards towards the centre of a disc or more or less perpendicular thereto.

It may be beneficial to include a pulse giving increased flow for over-coming inter-channel variations in flow resistance, in particular when initiating flow and/or when the liquid is to pass through branchings and curvatures.

The Sample.

The sample applied to an inlet port may contain one or more analytes, which may comprise lipid, carbohydrate, nucleic acid and/or peptide structure or any other organic structure. The analyte may also comprise an inorganic structure. The sample treatment protocol to take place within the microchannel structure typically means that the sample is transformed to one or more MS-samples in which (a) the MS-analyte is a derivative of the starting analyte and/or (b) the amount(s) of non-analyte species have been changed compared to the starting sample, and/or (c) the relative occurrence of different MS-analytes in a sample is changed compared to the starting sample, and/or (d) the concentration of an MS-analyte is changed relative the corresponding starting analyte in the starting sample, and/or (e) sample constituents, such as solvents, have been changed and/or the analyte has been changed from a dissolved form to a solid form, for instance in a co-crystallised form.

Item (a) includes digestion into fragments of various sizes and/or chemical derivatization of an analyte. Digestion may be purely chemical or enzymatic. Derivatization includes so-called mass tagging of either the starting analyte or of a fragment or other derivative formed during a sample treatment protocol, which takes place in the microchannel structure. Items (b) and/or (c) include that the sample analyte has been purified and/or concentrated. Items (a)–(d), in particular, apply to analytes that are biopolymers comprising carbohydrate, nucleic acid and/or peptide structure.

The sample is typically in liquid form and may be aqueous.

The sample may also pass through a microchannel structure without being changed. In this case the processing within a microchannel structure only provides a form for dosing of the analyte to the mass spectrometer.

FIGURES

Figure 2:
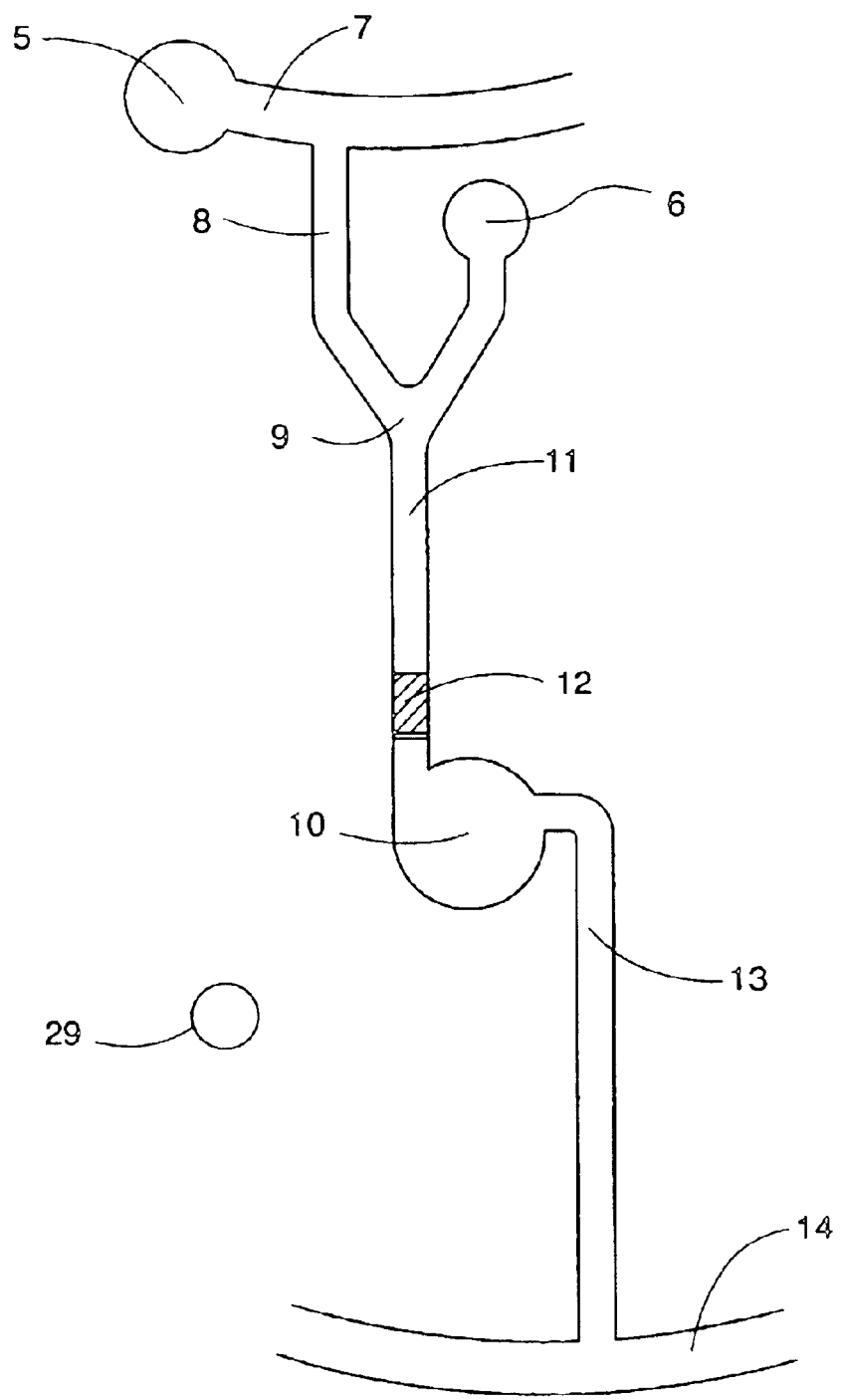
Figure 3:
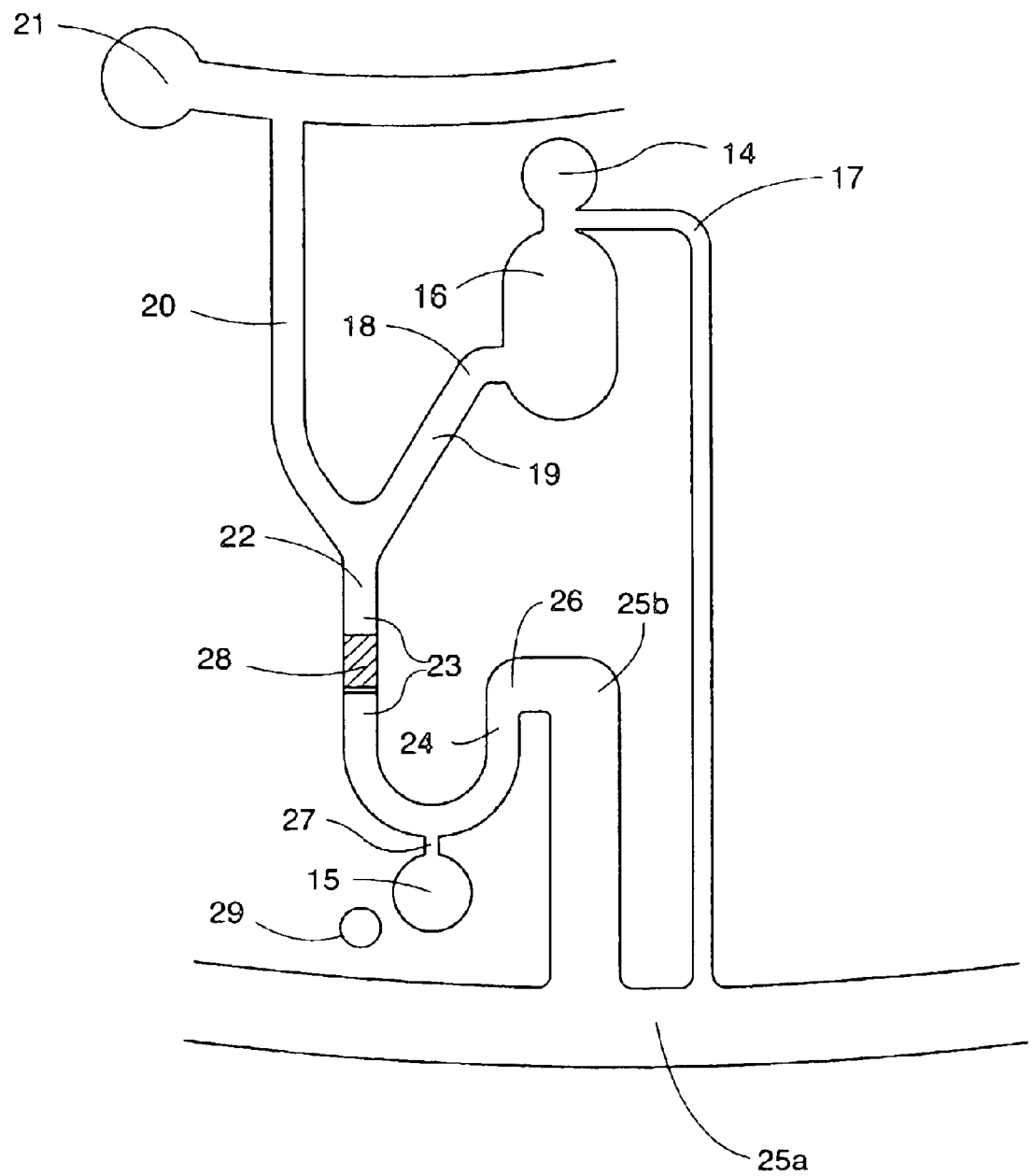

FIGS. 1–3 illustrate various microchannel structures that have an MS-port.

FIGS. 4a–f illustrate various designs and positions of the conductive layer (I) in MS-ports containing an EDI-surface (cross-sectional sideview of two MS-ports).

Figure 5:
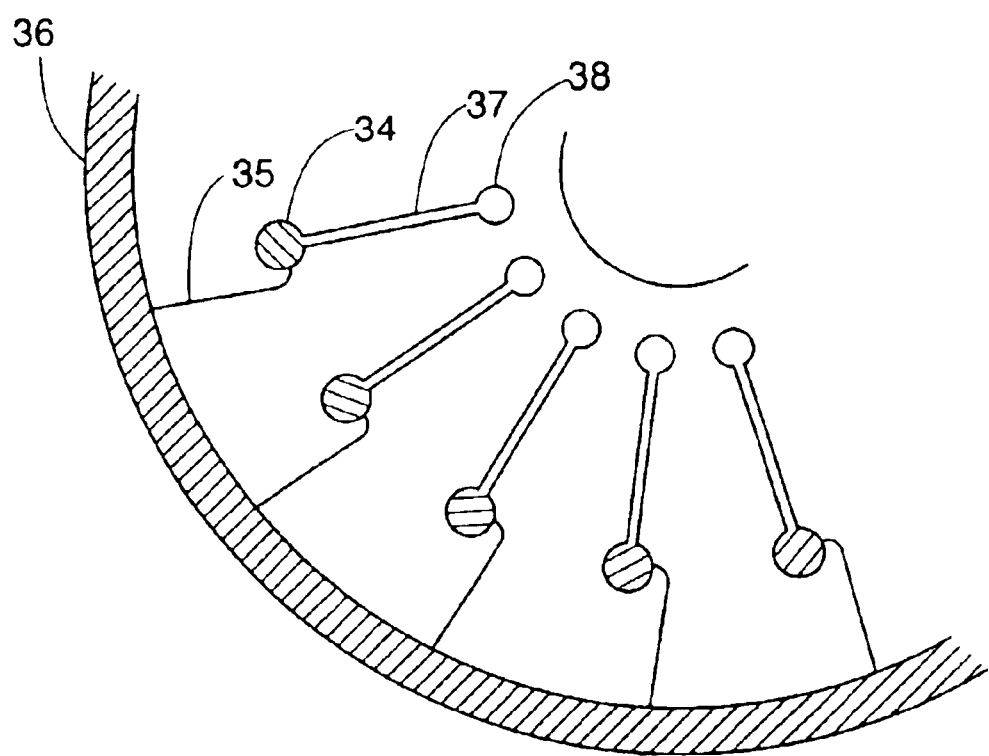

FIG. 5 illustrates an arrangement around EDI MS-ports with layer (I) and conductive connections (transparent lid, seen from above).

Figure 6A:
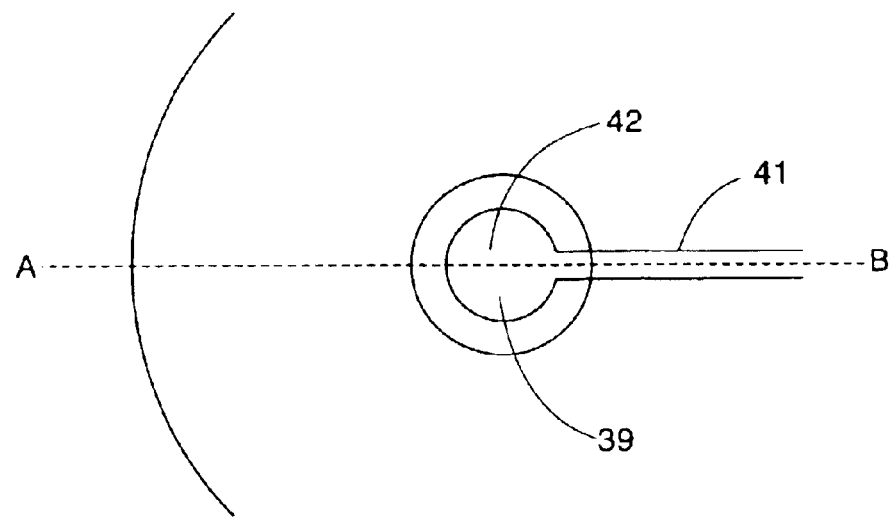
Figure 6B:
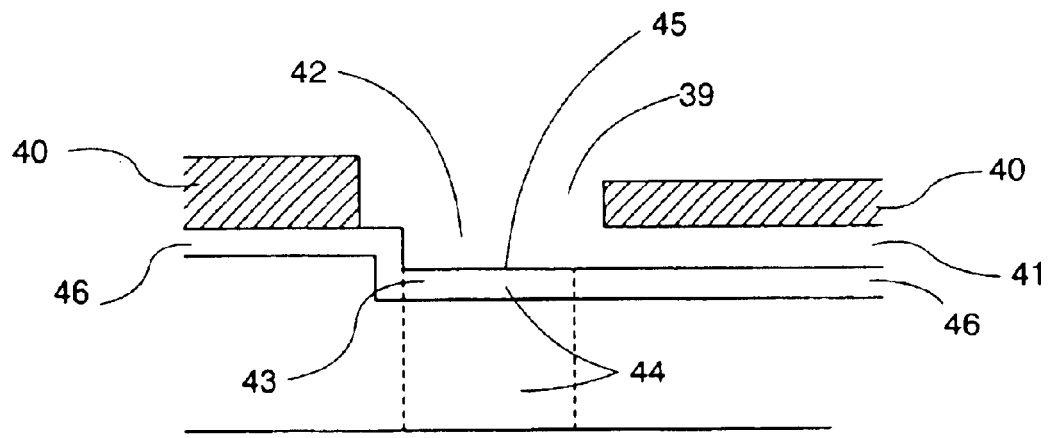

FIGS. 6a–b illustrate a variant of an EDI-port with a transparent lid (seen from above and in a cross-sectional side-view, respectively).

Figure 7A:
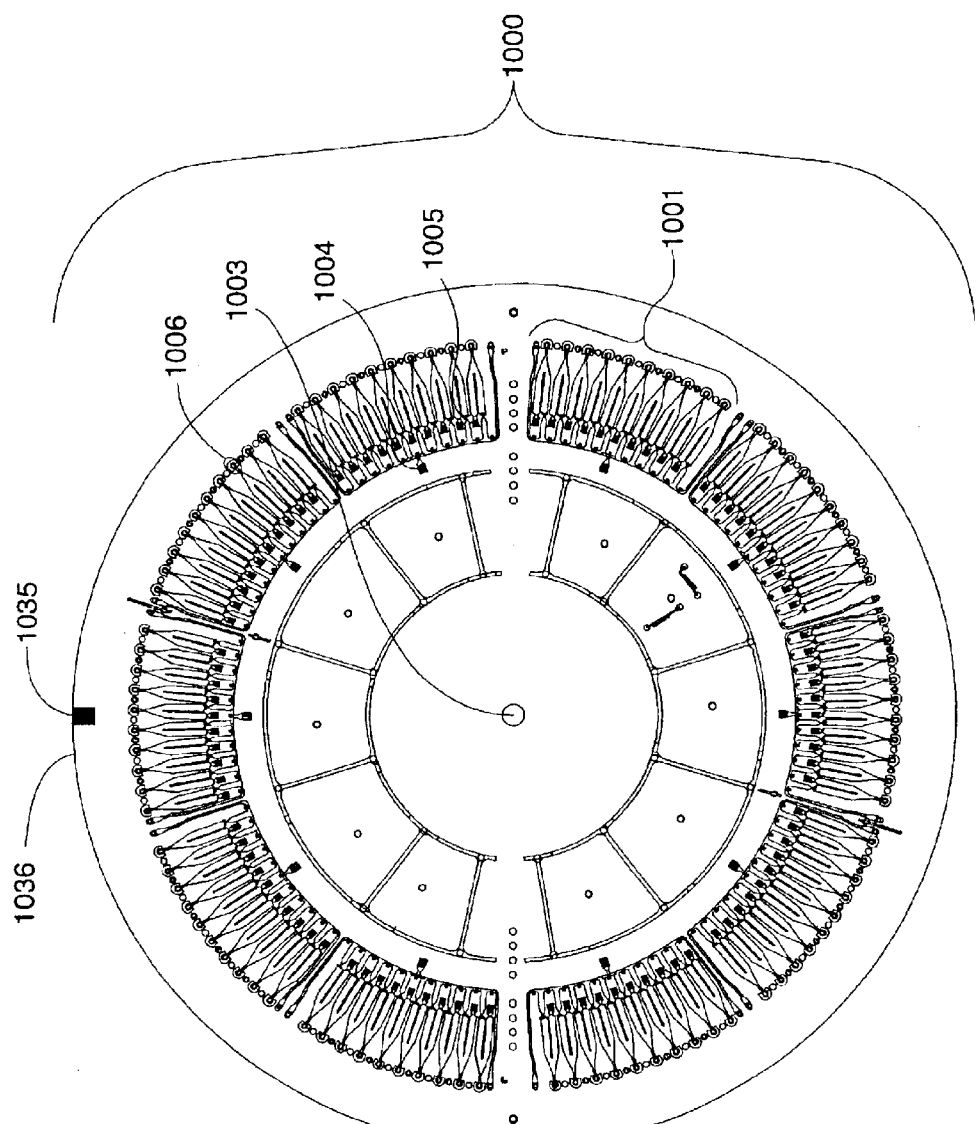

FIGS. 7a–b illustrate a variant of microchannel structures suitable to be interfaced with MALDI MS and an optimal arrangement on a full circular microfluidic disc (CD).

The microchannel structures of FIGS. 1–3 and 6–7 are fabricated in a planar substrate of a microfluidic substrate.

THE MICROFLUIDIC DEVICE.

The Microfluidic Structure

The microfluidic device comprises one or more microchannel structures having an inlet port for application of a liquid sample and an MS-port for release and presentation of an MS-analyte to a mass spectrometer. These kinds of ports may coincide in a microchannel structure. There may also be separate inlet ports for application of solvents and reagents and separate outlet ports or waste chambers/cavities for withdrawal of other components that are added and/or produced in the structure. Two or more microchannel structures may have a common inlet port. Depending on the particular design of the device some of the ports may be closed during the sample treatment but opened later on, for instance in order to enable proper release and presentation of the MS-analyte.

The distance between two opposite walls in a microchannel is typically $\leq 1000$ μm, such as $\leq 100$ μm, or even $\leq 10$ μm, such as $\leq 1$ μm. Functional channel parts (chambers, cavities etc) typical have volumes that are $\leq 500$ μl, such as $\leq 100$ μl and even $\leq 10$ μl such as $\leq 1$ μl. In important variants these volumes may be $\leq 500$ nl such as $\leq 100$ nl or $\leq 50$ nl. The depths of these parts may be in the interval $\leq 1000$ μm such as $\leq 100$ μm such as $\leq 10$ μm or even $\leq 1$ μm. The lower limits (width and depth) are always significantly greater than the largest of the reagents and analytes (including fragments and derivatives) that are to be transported within the microchannel structure. The lower limits of the different channel parts are typically in the range 0.1–0.01 μm. The aspect ratio (depth to width) may be $\geq 1$ or $\leq 1$ in all parts or in only a part of a microchannel structure.

Preferred microfluidic devices typically comprise one, two or more, preferably more than 5, microchannel structures. In the preferred variants, the device is formed by covering a substrate surface exposing parts of the microchannel structures with a lid comprising the remaining parts, if any, of the microchannel structures. The lid will prevent or minimise undesired evaporation of liquids as well as facilitate transport of liquids.

A microchannel structure preferably extends in a plane that is common for several microchannel structures. In addition there may be other microchannels that extend in other directions, primarily perpendicular to the common plane. Such other microchannels may function as sample or liquid application areas or connections to microchannel structures that are not located in the common plane, for instance.

The microfluidic devices may be disc-formed and have various geometries, with the circular form being the preferred variant (CD-form). Other variants of discs like the circular form may have an axis of symmetry that is at least 3- or at least 6-numbered. Circular forms typically have radii (r) $\geq 10\%$ or $\leq 300\%$ of the radii of a conventional CD with the conventional CD-format being the preferred.

On devices having circular forms or other forms having an axis of symmetry, an MS-port typically is located at a larger radial distance from the axis of symmetry than an inlet port, a common distribution system/channel etc of a microchannel structure. In the case there are more than one inlet ports they may be placed at different radial distances from the axis of symmetry. The flow direction for each microchannel structure is from an inner application area (inlet port, common distribution system or channel etc) towards an outlet port, typically an MS-port, at the periphery of the disc. The microchannel structures may be arranged in the form of one or more concentric circles (annular/circular arrangements) around the axis of symmetry of a disc. The MS-ports in each circle are at the same radial distance from the axis of symmetry. By the term "radially directed microchannel structure" means that the microchannel structure has an inlet port or a common distribution unit that is closer to the spinning axis (axis of symmetry) than an outlet port, typically the MS-Port. The term does not take into account the design or direction of part structures.

Each microchannel structure may comprise parts that differ with respect to function. In addition to the inlet ports, MS-ports, transportation conduits/channels there may be one or more parts that function as (a) application zone/port for reagents and liquids other than sample liquid (second inlet port),
(b) additional MS-ports,
(c) reaction zone, for instance for derivatization of an analyte discussed above (digestion, tagging etc).
(d) pressure creating zone (for instance hydrostatic pressure),
(e) volume defining zone,
(f) mixing zone,
(g) zone for separating and/or concentrating and/or purifying the analyte or a derivative or fragment thereof, for instance by capillary electrophoresis, chromatography and the like,
(h) waste conduit/chamber/cavity (for instance in the form of an outlet port),
(i) zone for splitting a liquid flow, etc.

Each of these parts may have the same or different cross-sectional dimensions as a preceding and/or a subsequent part of the microchannel structure.

The sizes of the various parts (a)–(i) depend on number of factors, such as the sample, reagents used, washing, process protocol, desired sensitivity, type of mass spectrometer etc. Typical sizes are found in the range of 1 nl to 1000 $\mu$l, mostly below 1 $\mu$l such as below 500 nl or even below 100 nl such as below 25 or 10 nl (volume defining unit, reactor part, separation part etc). Repeated application of a liquid, e.g. a sample, a washing liquid, a desorption liquid etc to the same inlet port may replace the need for a larger volume defining unit.

Splitting of a liquid flow may be located to an upstream part and associated with the inlet so that a starting sample is divided in several aliquots, each of which is then processed in parallel within the device of the invention.

Except for the presence of an MS-port, useful microchannel structures have been described in a number of previous patent publications. See the background publications discussed above.

Between parts having different functions there may be valves that can be overcome by increasing the force driving the liquid flow. For variants utilizing spinning, this may for instance be accomplished by increasing the spinning and/or utilizing pressure built up within the structure due to addition of a new portion of liquid combined with spinning. See for instance WO 0040750 (Gyros A B) and WO 0146465 (Gyros A B). Valves may be based on capillary junctions (WO 9807019 (Gamera Bioscience)) or hydrophobic breaks (WO 9958245 (Gyros A B) or on thermal properties of the valve material. The latter kind of valves may be illustrated by so called sacrificing valves (WO 9853311 (Gamera Bioscience)) for instance containing a plug of wax-like material, or reversible valves, for instance containing a thermoreversible polymer in the form of a plug (WO 0102737 (Gyros A B)).

One kind of microchannel structures used according to the invention comprises a zone in which separation and/or concentration and/or purification of the analyte or an analyte-derived entity can take place. This zone is located either before or in the MS-port. Examples of analyte-derived entities are fragments and derivatives of the analyte. This kind of functionality may be particularly important for samples containing low concentrations of analytes, complex mixtures of analytes or high concentrations of interfering substances that may negatively affect the resolution and/or sensitivity of the MS-analysis. The principles utilized for separation, concentration, purification, derivatization, fragmentation etc in the invention are similar to those that are used in the life science area, e.g. separations based on size exclusion and/or on differences in binding to a ligand structure are applicable. Accordingly, a separation zone may contain a separation medium that is capable of binding the analyte or an analyte-derived entity but not the contaminants, or vice versa. The separation medium is typically in particle/bead form, the surface of the separation zone, or a monolithic plug (porous) that permits through flow. If the analyte or the analyte-derived entity becomes bound, a liquid having the proper desorption characteristics for the bound entity is subsequently allowed to pass through the zone whereupon the bound entity is released and transported downstream. This transport may be directly to the MS-port or to a zone in which a further preparation step is accomplished. Washing steps may be inserted between the sample liquid and the desorption liquid. The separation medium may be soluble or insoluble during the binding step. Soluble separation media are typically insolubilized after binding a desired substance. The principles are well-known in the field of macroscopic separations.

Binding as discussed in the preceding paragraph typically means affinity binding or covalent binding to the separation medium. Covalent binding is typically reversible, for instance by thiol-disulfide exchange. Affinity binding (=affinity adsorption) can be illustrated with:

(a) electrostatic interaction that typically requires that the ligand and the entity to be bound have opposite charges,
(b) hydrophobic interaction that typically requires that the ligand and the entity to be bound comprises hydrophobic groups,
(c) electron-donor acceptor interaction that typically requires that the ligand and the entity to be bound have an electron-acceptor and electron-donor group, respectively, or vice versa, and
(d) bioaffinity binding in which the interaction is of complex nature, typically involving a mixture of different kinds of interactions and/or groups.

Ion exchange ligands may be cationic (=anion exchange ligands) or anionic (=cation exchange ligands). Typical anion exchange ligands have positively charged nitrogen, the most common ones being primary, secondary, tertiary or quarternary ammonium ligands, and certain amidinium groups. Typical cation exchange ligands have negatively charged carboxylate groups, phosphate groups, phosphonate groups, sulphate groups and sulphonate groups.

Bioaffinity binding includes that the analyte or the analyte-derived entity is a member of a so-called bioaffinity pair and the ligand is the other member of the pair. Typical bioaffinity pairs are antigen/hapten and an antibody/antigen binding fragment of the antibody; complementary nucleic acids; immunoglobulin-binding protein and immunoglobulin (for instance IgG or an Fc-part thereof and protein A or G), lectin and the corresponding carbohydrate, etc. The term "bioaffinity pair" includes affinity pairs in which one or both of the members are synthetic, for instance mimicking a native member of a bioaffinity pair.

If the analyte in a sample has peptide structure or nucleic acid structure or in other ways has a pronounced hydrophobicity, the separation medium may be of the reverse phase type (hydrophobic) combined with using desorption liquids (eluents) that are organic, for instance acetonitrile u, isopropanol, methanol, and the like. Depending on the particular sample and the presence of analytes or analyte-derived entities, which have a common binding structure, a group-specific separation medium may be utilized. The separation medium may thus, like a reverse phase adsorbent, result in an MS-sample that has a reduced concentration of salt, i.e. in desalting.

In each microchannel structure there may be two or more separation zones utilizing the same or different principles such as size and charge. For amphoteric substances such as proteins and peptides the latter principle may be illustrated with isoelectric focusing.

After a separation step comprising binding to a separation medium the concentration of an analyte or an analyte-derived entity in the desorption liquid after passage of the separation medium is typically higher than in the starting sample. The increase may be with a factor $>10^0$, for instance in the interval $10^1$–$10^6$, such as $10^1$–$10^4$.

As already mentioned a separation zone may be combined with zones for derivatization including fragmentation. There may also be microchannel structures that have a derivatization zone but no separation zone.

U.S. Ser. No. 60/322,621 and the corresponding International Application WO 02075312 describes the use of the above-mentioned affinity principles in an assay without explicitly referring to mass spectrometry.

FIG. 1 illustrates a microchannel structure that comprises (a) an inlet port (1) for liquids including the sample liquid, (b) an MS-port (2) comprising an EDI-surface, (c) a flow conduit (3) between the inlet port (1) and the MS-port (2). The MS-port may be open or covered. The flow conduit (3) may have a zone (4) containing an adsorbent for separation/concentration. If there are several microchannel structures in a device there may be a common application area/channel with openings for the inlet ports (not shown).

The structure of FIG. 1 may be present on a circular disc with the inlet port (1) closer to the centre than the MS-port (2). When transporting liquids through the conduit (3) by spinning the disc, liquid will leave the MS-port either as drops or by evaporation depending on the vapour pressure of the liquid and/or the spinning speed. A lower vapour pressure and an increased spinning speed will promote drop formation while a higher vapour pressure and a decreased spinning speed will promote evaporation of the liquid and crystallisation of the MS-analyte in the mS-port. A too low spinning speed and a too low vapour pressure will increase the risk for deposition of material in the conduit (3).

FIG. 2 illustrates another variant of a microchannel structure. It has two inlet ports (5,6) that may be used for application of sample, washing liquid and desorption liquid. One of the inlet ports (5) is connected to an application area/channel (7) that may be common to several microchannel structures in the same device. This first inlet port (5) is connected to one of the shanks (8) of a U-shaped channel via the application area/channel (7). The other inlet port (6) is connected to the other shank of the U. In the lower part of the U there is an exit conduit (9) leading to an MS-port (10). The exit conduit (9) may comprise a zone (12) containing a separation medium. From the MS-port (10) there may be a waste channel (13) leading to a waste channel (14) that may be common for several microchannel structures in the same device. Conduit (9) may comprise a valve function, for instance in the form of a hydrophobic break, upstream a possible separation zone (12).

The microchannel structure of FIG. 2 is also adapted to a circular disc and driving liquid flow by spinning the disc. The application channel (7) is at a shorter radial distance from the centre of the disc than waste channel (14).

FIG. 3 illustrates a microchannel structure which comprises a separate sample inlet port (14), an MS-port (15) and therebetween a structure that may be used for sample preparation. In this variant there is a volume-defining unit comprising a metering microcavity (16) between the sample inlet port (14) and MS-port (15) with an over-flow conduit (17) that ends in a waste chamber (25a) that may be common for several microchannel structures. At the lower part of the metering microcavity (16) there is a first exit conduit (18) leading to one of the shanks (19) of a U-shaped channel. The other shank (20) of this U may be connected to an inlet port (21) for washing and/or desorption liquids. At the lower part of the U-shaped channel there may be a second exit conduit (22) leading into one of the shanks (23) of a second U-shaped channel. The other shank (24) may be connected to a waste channel (25b) that after a bent (26) may end in a waste chamber (25a). At the lower part of the second U-formed channel there may be a third exit conduit (27) leading into the MS-port (15) that contain the EDI-surface. In order to control the flow in the microchannel structure, valve functions may be located
(a) in the first exit conduit (18), for instance immediately downstream the volume-defining unit (16),
(b) possibly also in the second exit conduit (22), for instance immediately after the first U,
(c) in the third exit conduit (27), for instance immediately after the second U, and
(d) in association with the connection between the over-flow channel (17) and the waste chamber (25a).

The valves may be of the types discussed above with preference for hydrophobic breaks. A suitable adsorbent (28) as discussed above may be placed in the second exit conduit (23) and may also function as a valve. In the case the adsorbent is in the form of particles they are preferably kept in place by a constriction of the inner walls of the conduits.

The structure presented in FIG. 3 is adapted for transporting liquid with centrifugal forces, i.e. with the structure present in a disc and oriented radially outwards from the centre of the disc. At the start of an experiment the metering cavity (16) is filled up with sample liquid at least to the connection between the over-flow channel (17) and the metering cavity (16), for instance by capillary action overflow channel (17). By first overcoming the valve function between the overflow channel (17) and the waste chamber (25a), excess liquid will pass into the waste chamber (25a). By then overcoming the valve function in the first exit conduit (18), the liquid in the metering microcavity (16) will pass into the first U and down through the adsorbent (28) where the analytes are captured. The liquid now being essentially devoid of analyte will then halt at the bottom of the second U. In the next step, one or more aliquots of a washing liquid may be applied through either of the inlet ports (14,21), i.e. through the second shank (20) of the first U or via the same inlet port (14) as the sample. A washing liquid will pass through the adsorbent (28), collect in the bottom of the second U and push the liquid already present into the waste chamber/channel (25a,b). Subsequently, a desorption liquid is applied through either of the two inlet ports (14,21) and passed through the adsorbent (18) where it releases the analyte and into the bottom of the second U where it pushes the washing liquid into the waste chamber/channel (25a,b). The desorption liquid containing released analyte is then passed into the MS-port (15) from the bottom of the second U by overcoming the valve function in the third exit conduit (27).

The operations are preferably carried out while spinning the disc. If the valves are in the form of hydrophobic breaks they can be passed by properly adapting the g-forces, i.e. by the spinning. By properly balancing the hydrophilicity/hydrophobicity of a liquid, passage or non-passage through a valve may be controlled without changing the spinning speed. This is illustrated by utilizing a hydrophobic break as the valve in the third exit conduit (27) combined with utilizing water-solutions as samples and washing liquids and liquids containing organic solvents as desorption liquids. In the alternative, valves that are opened by external means can be used. By placing the outlet of the first exit conduit (18) at a shorter radial distance from the centre of the disc than the lowest part of the metering microcavity (16) particulate matters, if present in the sample, will sediment and be retained in the volume-defining unit when the metering microcavity (16) is emptied through the first exit conduit (18).

Calibrator areas (29) are shown in each of FIGS. 1–3. Each calibrator area may be connected to a common area for application of a calibrator substance.

These kind of flow systems has been described in WO 0040750 (Gyros A B) and WO 0146465 (Gyros A B) which are hereby incorporated by reference.

In certain variants the inlet port for the sample and the MS-port may coincide. In this case the MS-port preferably comprises the surface on which the analyte can be collected (adsorbed). Remaining liquid and washing liquids, if used, are passed into the microchannel structure that then will function as a waste channel and possibly contain a separate outlet port particularly adapted for wastes and the like, or a waste chamber. In order to accomplish a concentrating and/or separating effect the surface may expose structures selectively binding/capturing the analyte as discussed above for a separation zone. This variant also encompasses that there may be a separate inlet port for washing and desorption liquids and microchannel part communicating with the combined sample and MS-port.

MS-ports

The MS ports may be adapted to different EDI mass spectrometry variants, for instance Time of Flight (TOF), Quadropole, Fourier-Transformed Ion Cyclotron Resonance (FT-ICR), ion trap etc.

The MS-port requires a free passage for the release of the ions created during desorption/ionisation and thus has an opening straight above the EDI-surface. The opening should be coaxial with and cover the EDI-surface. In other words the MS port is typically in form of a well or a depression with the EDI-surface at the bottom and in fluid communication at least with upstream parts of the corresponding microchannel structure. This includes that the opening may be covered during the sample treatment within the microfluidic device but subsequently opened to enable desorption/ionisation and possibly also evaporation of solvents. If an IDI principle is used the opening should also provide space for the incident irradiation.

An EDI-surface may in principle have any geometric form although preferred forms should be as compact as possible, for instance regular forms, such as squares and square-like forms, and rounded forms, such as circular and circle-like forms. The size of an EDI-surface preferably is the same as a circle with a diameter in the interval of 25–2000 µm. There may be advantages if the cross-sectional area of the incident beam used for irradiation is able to encompass the complete EDI-surface or as much as possible, for instance more than 25% or more than 50%.

An EDI-area comprises according to the invention a layer of conductive material (layer (I). The term conductive material includes semi-conductive material, although materials having a conductivity that is larger than silicon or larger than germanium are preferred. A typical conductive material comprise a) metals such as copper, gold, platinum etc, mixtures of metals (alloys), such as stainless steel etc b) conductive metal oxides and mixtures thereof, such as indium oxide, tin oxide, indium tin oxide etc, c) conductive polymers which includes polymers that are conductive as such and conductive composites containing a non-conductive polymer and a conductive material, for instance according to a)–c) and other conductive composites, etc.

Layer (I) has a conductive connection for supporting the proper voltage and charge transport at the EDI-surface.

Layer (I) is many times essentially planar and may coincide with the EDI-surface or be parallel thereto. The complete EDI-area from the lowest part to the EDI-surface may be made of conductive material, i.e. correspond to layer (I). In the case the microfluidic device comprises more than one microchannel structure with an MS-port, layer (I) of one EDI MS-port may be part of a common continuous conductive layer which extends into and encompasses layer (I) of two or more of the other EDI MS-ports. In preferred variants the common continuous layer comprises layer (I) of all EDI-MS ports of a microfluidic device. The common conductive layer may be essentially planar. The common conductive layer may have depressions corresponding to the EDI-surfaces and/or to other parts of the microchannel structures of the innovative device. Typical variants are that the common conductive layer is positioned (a) on top of the microfluidic device or (b) between two substrates that are joined together to form the enclosed microchannel structures of a microfluidic device.

In both variants the common conductive layer extends into the inner walls and layer (I) of the MS-ports. The MS-ports correspond to depressions.

The exact geometric shape of layer (I) outside the MS-port depends on the particular device and practical ways of its manufacture. For instance a common conductive layer may have an annular or arc-like form in case the MS-ports are annularly arranged.

In one innovative variant, the EDI-area has a non-conductive layer (layer (II)), which covers the conductive layer (I). Layer (II) in one EDI-area may extend into and encompass layer (II) in two or more of the other EDI-areas as described for layer (I).

In another innovative variant the device has a conductive layer (III) positioned above the common plane defined by the surface of each EDI-area of a device and not connected to layer (I) in different EDI MS-ports. Layer (III) has openings matching the EDI-surfaces and permitting irradiation of these surfaces and escape of ions through the openings.

These innovative variants of EDI-areas are schematically illustrated in FIGS. 4a–f, each of which shows a cross-sectional view across the EDI-areas of two MS-ports in a microfluidic device according to the invention. The EDI-surfaces are referenced as (51) and the EDI-areas as (52) (within the dotted vertical lines). Each MS-port comprises the EDI-area plus the corresponding depression. The conductive layers (53,54) are hatched. It is apparent that each EDI-area comprises a conductive layer (I) (53).

Figure 4A:
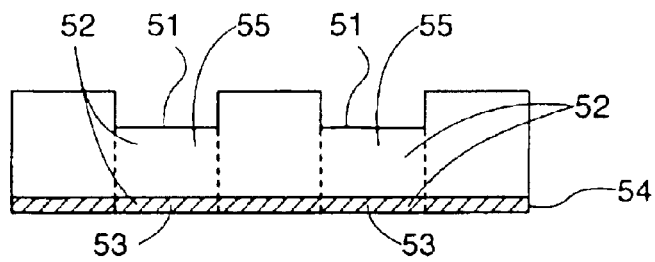
Figure 4B:
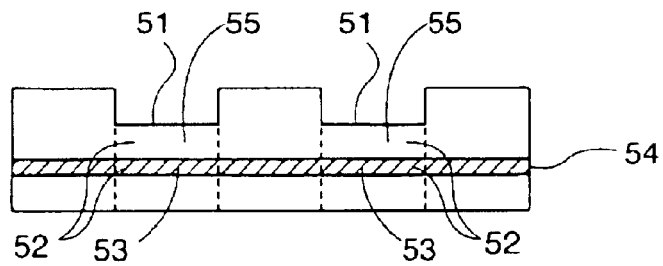
Figure 4C:
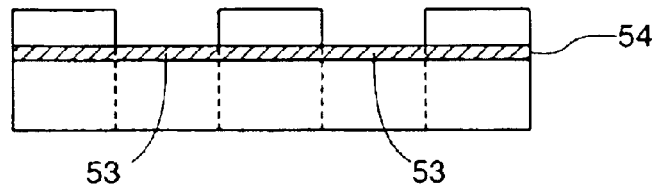
Figure 4D:
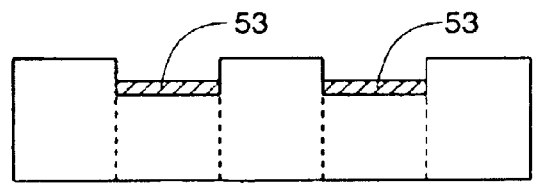
Figure 4E:
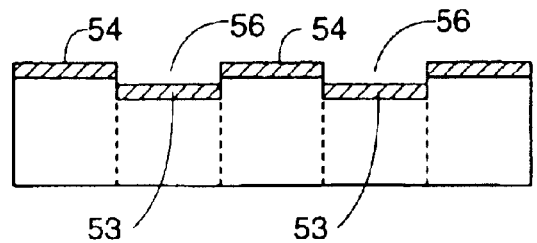
Figure 4F:
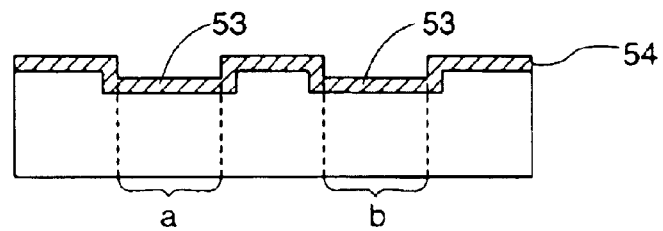

FIG. 4a shows a common continuous conductive layer (54) at the bottom of the device which layer encompasses layer (I) (53) of each EDI-area (52). A non-conductive layer (II) (55) is placed between layer (I) (53) and the EDI-surface (51). FIG. 4b shows a variant, which is similar to the variant in FIG. 5a, but the common continuous conductive layer is embedded within the device. Non-conductive layer (II) (55) is present. In FIG. 4c there is a common continuous conductive layer (54) comprising the EDI-surfaces and layer (I). In FIG. 4d there is no common continuous conductive layer. Layer (I) (53) for different MS-ports are isolated from each other and correspond to EDI-surfaces. FIG. 4e shows a variant in which there is a separate continuous conductive layer (54) above layer (I) (53) of the EDI areas. This conductive layer (54) has openings (56) corresponding to the openings of each MS-port and may be a surface layer on the upper or lower side of a lid covering the microchannel structures. FIG. 4f shows a variant in which there is a common continuous conductive layer comprising layer (I). The EDI-surfaces coincides with layer (I) in the MS-ports. The continuous layer also encompasses the inner walls of the MS-ports. The MS-ports appear as depressions in the common conductive layer.

For variants in which the open microchannel structures have been fabricated in a base substrate and covered by a lid, the base substrate may consist of conductive material and correspond to layer (I). In these variants the lid may comprise a non-conductive or conductive material.

FIG. 5 illustrates an arrangement of MS-ports on a circular disc (with a transparent lid), in which layer (I) (34) of each MS-port has a conductive connection (35) with a peripheral conductive layer (36) which is closer to the edge of the disc than the MS-ports. In this variant each microchannel structure (37) comprises an MS-port and extends upstream to an inlet port (38). Layer (I) (34), the connections (35) and layer (36) may be interpreted as a continuous conductive layer.

FIGS. 6a–b illustrate a MS-port in which the opening above an EDI-surface is defined by a hole (39) in a lid (40) which in this case is transparent. The incoming microchannel (41) opens to a circular depression (42) with a diameter, which is less than the diameter of the hole (39). Layer (I) (43), EDI-area (44), EDI-surface (45) are between the two dotted lines. Layer (I) extends into a common conductive layer (46). This design in which the MS-port provides an opening which is greater than the EDI area will facilitate for an incident beam to cover any spot of the EDI surface. In preferred variants the microchannel (41) extends into the bottom of the MS-port as an open microchannel of constant depth. Seen from above the microchannel may be widening like an expanding droplet.

A conductive layer per se may function as a conductive connection or there may be distinct connections (35) to layer (I). See FIG. 5.

In certain variants the lid that covers the microchannel structures also covers the EDI-surfaces. For these variants the lid is removable at least at the MS-ports. After processing of a sample in an upstream part of a microchannel structure and transportation of the treated sample to the covered MS-port, the lid is removed thereby permitting evaporation of solvents from the MS-port and irradiation in order to accomplish desorption/ionisation of MS-analyte molecules.

Liquids in the MS-ports.

During transport through a microchannel structure the solvent composition may be changed to fit the particular kind of mass spectrometer used. In the case of microchannel structures comprising EDI MS-ports and separation zones containing a separation medium, a compound (=EDI-matrix) that upon co-crystalisation with the analyte or analyte-derived entity assists desorption/ionisation may be (a) included in the desorption liquid, (b) included in another liquid that is also guided to the MS-port, or (c) predispensed to the EDI-surface or dispensed to this surface after the analyte or analyte-derived entity has been deposited on the EDI-surface. There may also be included compounds that facilitate crystallization on the EDI-surface. Both kinds of helper compounds may be included even if there is no separation zone.

Calibration of the Mass Scale.

To ensure accurate mass determination, calibrator areas (spots) containing a compound of known molecular weight (standard, calibrator substance) may be present in the proximity of an MS-port. Calibrator areas (29) are shown in FIGS. 1–3. Alternatively, the standards may be included in the sample or added to an EDI-area before desorption/ionisation (internal calibrator). The choice of calibrator substance, its amount etc will depend on its use as an external or internal calibrator, the MS-analyte and its concentration etc.

Material From Which the Microfluidic Device is Manufactured.

The microchannel structures are typically fabricated in inorganic and/or organic material, preferably plastics or other organic polymers. The material may be conductive or non-conductive as already discussed. Certain parts of a microchannel structure may be metalized.

Suitable organic polymers may derive from polymerisation of monomers comprising unsaturation, such as carbon-carbon double bonds and/or carbon-carbon-triple bonds. The monomers may, for instance, be selected from mono-, diand poly/oligo-unsaturated compounds, e.g. vinyl compounds and other compounds containing unsaturation.

Another type of organic polymers that may be used is based on condensation polymers in which the monomers are selected from compounds exhibiting two or more groups selected among amino, hydroxy, carboxy etc groups. The plastics contemplated are typically polycarbonates, polyamides, polyamines, polyethers etc. Polyethers include the corresponding silicon analogues, such as silicone rubber.

The polymers are preferably in cross-linked form.

The plastics may be a mixture of two or more different polymer(s)/copolymer(s).

At least a part of the microchannel structure may have a surface that has been derivatised and/or hydrophilized, for instance by being coated with a non-ionic hydrophilic polymer according to the principles outlined in WO 0147637 (Gyros A B) or by treatment in gas plasma. Typical gas plasma treatments utilize non-polymerisable gases, for instance as outlined in WO 0056808 (Gyros A B). A hydrophilized surface may also be funtionalized in order to introduce one or more functional groups that are capable of interacting with the sample analyte, an analyte-derived compound or one or more of the reagents added. Surfaces may be made of copper, gold, platinum, stainless less etc, for instance by metallization, in order to enable a desired derivatization or for providing a conductive surface, for instance in an MS-port. Gold surfaces for instance may be derivatized by reaction with thiol-containing compounds that have a desired functionality, for instance hydrophilicity.

The optimal water contact angle for the surfaces within a structure depends on the protocols to be carried out, the dimensions of the microchannels and chambers, composition and surface tension of the liquids, etc. As a rule of thumb, the surface of one, two, three or four of the inner walls (side-walls, bottom or top), of a microchannel in a microfluidic device have to be wettable by the liquid used, preferably aqueous liquids, such as water. Preferred water contact angles are $\leq 40°$ or $\leq 30°$, such as $\leq 25°$ or $\leq 20°$. These figures refer to values obtained at the temperature of use, primarily room temperature.

It is believed that the preferred variants of the inventive microfluidic devices will be delivered to the customer in a dry state. The surfaces of the microchannel structures of the device therefore should have a hydrophilicity sufficient to permit the aqueous liquid to be used to penetrate different parts of the channels of the structure by capillary forces (self-suction). This of course only applies if a valve function at the entrance of the particular part has been overcome.

Best Mode

The best mass spectrometric results accomplished at the priority date have been obtained for the variant described in example 4 below.

The best mode at the filing date is illustrated by example 5.

The invention is further defined in the appending claim and will now be illustrated with a non-limiting experimental part.

The following patents and patent applications have been referenced in this specification and hereby incorporated by reference:

WO 9116966 (Pharmacia Biotech A B), WO 9721090 (Gamera Bioscience), WO 9807019 (Gamera Bioscience) WO 9853311 (Gamera Bioscience), WO 9955827 (Gyros A B), WO 9958245 (Gyros A B), WO 0025921 (Gyros A D), WO 0040750 (Gyros A B), WO 0056808 (Gyros A B), WO 0062042 (Gyros A B), WO 0102737 (Gyros A B), WO 0146465 (Gyros A B), WO 0147637, (Gyros A B), WO 0154810 (Gyros A B), WO 0147638 (Gyros A B), WO 0185602 (Åmic AB & Gyros A B), and U.S. Ser. No. 60/322,621 and corresponding International Applications. WO 02074438 (Gyros A B) and WO 02075312 (Gyros A B), respectively.

EXPERIMENTAL PART

Example 1

Gold at Different Positions in a CD

| Gold patterning | Sensitivity* | Charging of substrate** |
|---|---|---|
| No gold | Poor | Yes |
| Gold on all sides | Good | No |
| Gold on upper side | Good | No |
| Gold on bottom side | Good | Yes |
| Isolated gold spots on the upper side | Good | Yes |
| Gold spots on the upper side. Every spot being conductively connected contact with the adapter plate through an individual gold string or a common gold area. | Good | No |

*Good = sensitivity for an in-solution tryptic digest of BSA comparable to the sensitivity obtained on a conventional stainless steel target
**Charging is observed as significant mass shift ($\geq 1$ Da) upon repeated laser desorption/ionization and/or loss of signal.

This table shows the results form a summary of experiments performed before the priority date in order to optimise the design of the CD-MALDI interface. Gold was sputtered at various positions of the CD and the MALDI characteristics were studied for a tryptic digest of Bovine Serum Albumin (BSA). The CD was placed on a metal adapter inserted into the ion source. The gold was hence patterned in various ways to determine the importance of electrical contact between the MALDI ports and the adapter plate.

Example 2

Planar CD and Structured Removable Lid

This example shows a planar CD in combination with a lid in which the microfluidic structures are present. The structured lid was achieved through casting Memosil (Hereaus, Germany) against a nickel-coated master. The microfluidic structure employed in this example is shown in FIG. 2.

The structured lid is attached to the CD by adhesion forces. The surface facing the lid should be hydrophilic as the presented invention utilizes capillary action to fill the microfluidic structures. This is especially important as the moulded lid, being a type of silicon rubber is hydrophobic.

The upper side of the CD was covered with gold using a DC Bias magnetron sputtering method (1* 10–5 torr, Ar plasma and titan as adhesion layer) and made hydrophilic according to the following procedure; The gold sputtered side was cleaned by rinsing with ethanol, followed by an oxygen plasma treatment (Plasma Science PSO500,). After plasma cleaning a self-assembled monolayer (SAM) of hydroxylthiol was formed on the gold surface. The hydroxylthiol was 11-mercapto-1-undecanol (Aldrich, Milwaukee, Wis.) and used at a concentration of 2 mM in degassed ethanol. To obtain a well-organized SAM, the gold sputtered disc was immersed in the thiol solution over night. After the thiol adsorption the CD was sonicated in ethanol for ca 2 min.

The lid, containing the microfluidic channels, was attached to the CD by adhesion forces. A second piece of polymeric material was mounted at a position of 180° from the structured lid as a counterbalance. Reversed phase beads (Source 15 RPC, Amersham Pharmacia Biotech, Sweden) with a diameter of 15 µm were packed into the individual structures using the filling port present in the common distribution channel. The slurry, containing the beads, was drawn into the individual channels by capillary action. Eighteen parallel reversed phase columns were formed when the disc was spun at 3000 rpm for 1 minute. The columns were rinsed with water containing 0.1% TFA (trifluoroacetic acid, Aldrich)) two times. The rinsing was performed at an rpm of 2500 for ca 1 min. 200 nL of in-solution tryptic digest of BSA was added to individual channels through the sample inlet. The following procedure was used for digestion. The BSA (Sigma) was dissolved to a final concentration of 4.75 pmol/µl in 0.1 ammonium bicarbonate buffer at pH8. The enzyme-modified trypsin (Promega Corp., Madison, Wis.) was added and dissolved at a ratio of BSA/trypsin 20:1. The sample was incubated at 37° C. for 4 hours and then stored at −20° C. until used.

The sample was allowed to pass over the reversed phase columns at 1500 rpm. A second rinsing/washing step was performed as above using water containing 0.1% TFA. Finally the peptides were eluted using 200 nL eluent consisting 50% isopropanol, 50% water and α-cyano-4-hydroxycinnamic acid (Aldrich) below saturation. The eluent was prepared by saturating a water:isopropanol (50%) mixture with α-cyano-4-hydroxycinnamic acid. To 100 µL of this mixture 200 µL of 50% water:50% isopropanol was added, resulting in an eluent saturated to approximately $\frac{2}{3}$ with α-cyano-4-hydroxycinnamic acid.

The presentation of the sample in the MALDI port was performed in two different ways.

a) In the first example a full structure was utilised (FIG. 2). Eluent from the column was collected in the container placed at an outer radial position relative of the reversed phase column. When the lid was removed the liquid quickly evaporated leaving co-crystallized matrix and peptides on the gold sputtered surface. The disc was cut in halves to fit in the MALDI ionisation interface.

b) The moulded structure was cut directly after the packed column leaving an open-ended microstucture. The eluent was allowed to pass the column at a pre-determined speed (1500 rpm) in order to generate a controlled evaporation of the solvent at the MALDI port, and hence the formation of co-crystallized matrix and peptides suitable for MALDI analysis. The disc was cut in halves to fit in the MALDI ionisation interface.

Example 3
Structured CD and Site-specific Elution

This example employs a CD with integrated microfluidic structures, a thin (≦70 µm) lid with holes at positions matching the MALDI port in the CD. The microfluidic structure employed in this example is shown in FIG. 1.

The polycarbonate CD was covered with gold as described above. The side was hydrophilized using the thiolprocedure described above. The lid (SkultunaFlexible, Skultuna, Sweden), having, pre-drilled holes, was attached to the CD through heat pressing at 135° C.

Reversed phase beads (Source 15 RPC) with a diameter of 15 µm were packed in the individual structures using capillary forces in combination with centrifugation. The columns were rinsed with ethanol and spun to dryness before 23 fmol of tryptically digested BSA was added and spun down using 700 rpm. The tryptic digest of BSA was generated according to the procedure described above. After sample addition, the column was rinsed twice with water. α-cyano-4-hydroxycinnamic acid was mixed in an organic solvent of acetonitrile/water 3:7 containing 0,1% TFA to a saturation of $\frac{2}{3}$ and 250 nl was used to elute the sample from the 3 nl packed column.

The crystals obtained after evaporation of the organic/water mixture contained co-crystallized peptides. Eight singly charged peptide peaks were present in the mass spectrum obtained.

Example 4
Parallel Sample Preparation in a Product CD.
Description of the Microfluidic Disc (CD)

FIG. 7a illustrate a product microfluidic device (CD) (1000) comprising 10 sets (1001) of identical microchannel structures (1002) arranged annularly around the spinning axis (axis of symmetry) (1003) of a circular disc (1000). Each set comprises 10 microchannel structures. Each microchannel structure is oriented radially with an inlet port (1004,1005) located at shorter radial distance than an outlet port (MS-port) (1006). The MS-ports are ~0.9 cm from the edge of the disc (not shown). The disc was of the same size as a conventional CD. The CD has a home mark (1035) at the edge (1036) for positioning the disc when dispensing liquids.

The final device comprises a bottom part in plastic material that contains the uncovered form of the microchannel structures given in FIG. 7a. The microchannel structures are covered with a lid in which there are circular holes (1007,1008,1009,1010,1011,1012 in FIG. 7b) that will function as inlets (1007,1008) or outlets (1009,1010) in the final microfluidic device or as separate claibrator areas (1011, 1012). The bottom part with its microstructures is made of plastics and has been manufactured by a moulding replication process. The surface with the uncovered form of the microchannel structures has been hydrophilised in accordance WO 0056808 (Gyros A B). The lid was thermo laminated to the bottom part in accordance with WO 0154810 (Gyros A B).

FIG. 7b shows in enlarged form a set (1001) of 10 microchannel structures (1002). Each microchannel structure has a sample inlet port (1005) and one common inlet port (1004) for other liquids. At the bottom of each of these two inlet ports (1004,1005) there are ridges/grooves (1013) directed inwards the microchannel structure. The sample inlet port (1005) is connected to one (1014) of two inwardly/upwardly directed shanks (1014,1015) of a Y-shaped sample reservoir (1016). The inlet port (1004) for other liquids is common for all microchannel structures in a set and is connected to a common distribution manifold (1017) with one reservoir/volume defining unit (1018) for other liquids than sample connected to the other upwardly directed shank (1015) of each sample reservoir (1016). The distribution manifold (1017) has one waste outlet port (1009) at each flank of the set. The downward shank (1019) of the Y-like sample reservoir (1016) leads to an outlet port (MS port) (1006) and comprises a bed (1020) of chromatography particles (RPC, reversed phase chromatography) held against a dual depth (1021) (from 100 µm to 10 µm to 20 µm in the flow direction), of the outer part of the downward shank/microchannel (1019). The microchannel corresponding to the downward shank (1021) will end in the bottom (1022) of the outlet port (MS port) (1006) as a widening groove (drop-like seen from above)(1023), which will function as a crystallization area.

Each volume-defining unit (1018) for other liquids is surrounded by anti-wicking means (1024,1025) that will prevent wicking of liquid between the volume-defining units (1018). The anti-wicking comprises both (a) a geometric change (1024) in edges going between the volume defining units (1018) or from a volume defining unit (1018) to a waste outlet port (1009) and a hydrophobic surface break (1025, rectangle).

Valve functions in the form of local hydrophobic surface breaks (rectangles, 1026, 1027) are present in the waste channels (1028) of the distribution manifold (1017) before the outlet openings (1009) at the flanks, and in each microconduit (1029) between a volume defining unit (1018) for other liquids and the upwardly directed shank (1015) of the sample reservoir (1016). The valve function (hydrophobic surface break) (1027) may be positioned before, across or immediately after the joint between the microconduit (1029) and the upward shank (1015) of the sample reservoir (1016). Despite the sharp change in lateral dimension at the joint between the microconduit (1029) and the upward shank (1015), the hydrophobic surface break (1027) was imperative for the valve function.

Local hydrophobic surface breaks (1030,1031, rectangles) for directing liquid into the structure are present at the inlet openings (1007,1008).

Furthermore, a U- (horse-shoe) shaped local hydrophobic surface break (1032) is positioned at the outlet opening (1010 of each outlet port (1006, MS-port) for preventing liquid exiting into the port from spreading onto the top of the disc. The hydrophobic surface breaks (1026,1027,1030, 1031) were applied before an upper substrate (lid) was laminated to the surface of the bottom substrate comprising the microchannel structures in open form. The hydrophobic surface break (1032) was applied after lamination and gold sputtering.

The openings (10011,1012) in the lid are calibration areas for calibration substance. The surface within the circles is the top of the bottom part. One (1012) of them comprises a depression (1033) that mimics the widening groove (1022) of an MS-port (1006)

Before application of the local hydrophobic surface area (1032) around the opening (1010) the top of the lid was sputtered with gold at least as a continuous layer in-, around-, and between the openings including the calibrator areas (1010). A continuous gold film thus were connecting the bottom and the walls of the MS-ports (1006) and the calibrator areas. Other parts of the lid (but not the whole lid), besides the areas in and around the MS-ports and calibrators, were also covered with gold. The aim has been to cover as much lid area as possible with gold as long as the gold layer do not interfere with microfluidic- and instrumental functions, e.g. the gold is not allowed to cover the rim of the lid (CD) as it upsets the home-positioning of the CD or the inlets (1007,1008) of the microfluidic structures since it affects the capillary force by an increased hydrophobicity (liquid would then be more difficult to fill up the channels). Other conducting materials than gold could also be beneficial for this application, for instance at the filing date indium tin oxide was sputtered onto the lid and was shown promising for this application. Since indium tin oxide is much more transparent than gold and relatively hydrophilic the whole lid could be covered (i.e. no mask would be necessary for sputtering the conductive layer) without concern for microfluidics and instrumental aspects. Therefore the manufacturing and production process would be more simple and cheap.

The depth in the microchannel structures is the same (100 $\mu$m) and constant from the inlet openings (1007,1008) to the dual depths (1021).

Loading of RPC-particles.

The distribution manifold (1017) is filled with a suspension of RPC-particles via the common inlet port (1004). After filling, the suspension will be present between the inlet port (1004) and the valves (1026) at the flanking waste openings (1009). Upon spinning at a first speed, excess waste suspension will leave the distribution manifold (1017) via the flank openings (1009) while air will enter the manifold (1017) via the flank openings (1009) while air will enter the manifold via the common inlet (1004). Defined aliquots (about 0.2 $\mu$l) of the suspension will be retained in the volume-defining units (1018). The anti-wicking means (1024,1025) surrounding the volume-defining units (1018) will assist in retaining the defined volume in each volume-defining unit. When the spinning speed is increased, the aliquots in the volume-defining units (1018) will break through the valves (1027), pass through upward shanks (1015) and the Y-shaped sample reservoirs (1016) and out through the downward shank (1019). The particles will be collected as a packed bed (1020) against the dual depth (1021), and the liquid will pass out through the outlet opening (1012) where it leaves the system.

Filling of the distribution manifold (1017) including the volume defining units (1018) through the common inlet port (1004) is solely by capillary force.

Experimental

A model protein consisting of bovine serum albumin (BSA) in 50 mM ammonium bicarbonate buffer, pH 8, was reduced and alkylated according to standard protocol and in-solution digested with trypsin. The reaction was quenched by adding trifluoroacetic acid (TFA) to a final concentration of 0.1% and transferred to a micro plate for subsequent sample processing on-CD, as described above.

Sample and reagents were transferred from micro plates (containing typical volumes of 5 to 100 $\mu$l) to CD by a robotic arm. The robotic arm holds 10 capillaries where sample and reagents are contained inside during transfer. The volume of sample/reagents aspirated into the capillaries and later dispensed onto the CD is driven by syringe pumps and controlled by software (as are the robotic arm). Aspiration and dispension rates are typical in the 0.5–10 $\mu$l/sec rate. Once the liquid is dispensed onto the CD, at respective inlet port, it is drawn, by capillary force, into respective microchannel structure.

The instrument for performing the experiment was a CD microlaboratory (Gyrolab Workstation, Gyros A B, Uppsala, Sweden). This instrument is a fully automated robotic system controlled by application-specific software. Microplates containing samples or reagents are stored in a carousel within the system. A high precision robot transfers samples from microplates or containers into the microworld of the CD. CDs are moved to the spinning station for the addition of samples and reagents. An application-specific method within the software controls the spinning at precisely controlled speeds controls the movement of liquids through the microstructures as the application proceeds. The CDs are transferred to a MALDI mass spectrometer for analysis and identification.

In order to reduce eventual carry-over between individual microchannel structures, i.e., if part of sample remains inside the capillary after dipensing it onto CD it might contaminate the sample following and has therefore to be properly washed away, the following wash procedure was applied:

1. 20 μl of water was flushed through all capillaries.
2. 4 μl of 50% ethanol in water was then aspirated into the capillaries and dispensed to waste, this was repeated four times using 4.5 μl in the last two cycles.
3. Finally, 4 μl of 0.1% TFA was aspirated and dispensed to waste, this was repeated four times using 4.5 μl in the last two cycles.

Operation Method

The following scheme gives an overview of a typical spin program for running multiplex samples on a CD for the above-mentioned MALDI application.

The CD is the one described above. A ramp (see below) indicates an acceleration phase, deceleration phase, or a constant rpm value.

The CD was applied in an instrument from Gyros A B.

1. First Spin.

The purpose here is to restore ("re-pack") the chromatographic columns.

| Order | Ramp (rpm) | Time (sec) |
|---|---|---|
| 1 | 7000 | 2 |
| 2 | 7000 | 30 |
| 3 | 0 | 2 |

2. Conditioning of Common/Individual Microstructures and Reversed-Phase Columns 3.8 μl(per 10 structures) of 50% acetonitrile in water is dispensed into each common inlet port (1004). The first ramp (no spin) is a lag period as for the liquid to completely fill up the common channel.

| Order | Ramp (rpm) | Time (sec) |
|---|---|---|
| 1 | 0 | 5 |
| 2 | 700 | 7 |
| 3 | 700 | 2.5 |
| 4 | 1600 | 0.15 |
| 5 | 1600 | 20 |
| 6 | 0 | 2 |
| 7 | 8000 | 2 |
| 8 | 8000 | 30 |
| 9 | 0 | 2 |

3. Conditioning of Individual Microstructures

This item differs from the one above (no 2) by addressing other parts of the microchannel structures not accessible by the procedure mentioned in item 2. The purpose is to more completely re-wett any microstructure. 400 nl of 50% acetonitrile in water is dispensed per microchannel structure through each inlet ports (1005).

| Order | Ramp (rpm) | Time (sec) |
|---|---|---|
| 1 | 8000 | 2 |
| 2 | 8000 | 30 |
| 3 | 0 | 2 |

4. Conditioning of Common/Individual Microstructures and Reversed-phase Columns 3.8 μl(per 10 structures) of 0.1% trifluoroacetic acid (TFA) in water is dispensed into each common inlet port (1004). The first ramp (no spin) is a lag period as for the liquid to completely fill up the common channel.

| Order | Ramp (rpm) | Time (sec) |
|---|---|---|
| 1 | 0 | 5 |
| 2 | 700 | 7 |
| 3 | 700 | 2.5 |
| 4 | 1600 | 0.15 |
| 5 | 1600 | 20 |
| 6 | 8000 | 2 |
| 7 | 8000 | 30 |
| 8 | 0 | 2 |

5. Sample Transfer

1–10 μl of sample is applied into each inlet port (1005) (total 100 identical micro structures and therefore 100 samples per CD). The first ramp (no spin) is a lag period as for the liquid to completely fill up the common channel.

| Order | Ramp (rpm) | Time (sec) |
|---|---|---|
| 1 | 0 | 5 |
| 2 | 1800 | 0.3 |
| 3 | 1000 | 0.2 |
| 4 | 1000 | 30 |
| 5 | 2000 | 0.2 |
| 6 | 1200 | 0.2 |
| 7 | 1200 | 20 |
| 8 | 2500 | 0.25 |
| 9 | 1500 | 0.2 |
| 10 | 1500 | 20 |
| 11 | 0 | 2 |

6. Desalting/Washing of Sample.

3.8 μl (per 10 structures) of 5–10% organic solvent/0.1% trifluoroacetic acid (TFA) in water is dispensed into each common inlet port (1004). The first ramp (no spin) is a lag period as for the liquid to completely fill up the common channel.

| Order | Ramp (rpm) | Time (sec) |
|---|---|---|
| 1 | 0 | 5 |
| 2 | 700 | 7 |
| 3 | 700 | 2.5 |
| 4 | 1600 | 0.15 |
| 5 | 1600 | 20 |
| 6 | 8000 | 2 |
| 7 | 8000 | 30 |
| 8 | 0 | 2 |

7. Sample Elution and Peptide-matrix Cocrystallization on MALDI Target Area on CD.

Eluent consists of 50% acetonitrile/0.1% TFA in water wherein the MALDI matrix (1.5 g/ml of α-cyanohydroxycinnamic acid) is dissolved. 4.1 μl of eluent (per 10 structure) is applied into each common inlet port (1004).

| Order | Ramp (rpm) | Time (sec) |
|---|---|---|
| 1 | 0 | 2 |
| 2 | 600 | 0.1 |
| 3 | 600 | 7 |
| 4 | 1400 | 0.14 |
| 5 | 1400 | 0.25 |

-continued

| Order | Ramp (rpm) | Time (sec) |
|---|---|---|
| 6 | 300 | 0.22 |
| 7 | 300 | 4 |
| 8 | 1400 | 0.2 |
| 9 | 1400 | 0.1 |
| 10 | 300 | 0.2 |
| 11 | 300 | 4 |
| 12 | 1400 | 0.2 |
| 13 | 1400 | 0.1 |
| 14 | 300 | 0.1 |
| 15 | 300 | 4 |
| 16 | 1600 | 0.2 |
| 17 | 1600 | 0.1 |
| 18 | 1200 | 0.07 |
| 19 | 1200 | 0.4 |
| 20 | 1000 | 0.05 |
| 21 | 1000 | 1 |
| 22 | 800 | 0.05 |
| 23 | 800 | 90 |
| 24 | 1200 | 0.1 |
| 25 | 1200 | 1.9 |
|  | 800 | 0.1 |
|  | 800 | 90 |
|  | 0 | 2 |

The CD (or more exactly half of it) was subsequently fixed to a steel target holder and inserted into a MALDI TOF instrument (Bruker Biflex) for running mass spectrometry.
Results The molecular mass of the peaks was identified as BSA peptides by a database search (NCBI). The mass spectra typically showed ten peaks which were identified as BSA peptides. High sensitivity was attainable using the CD for sample concentration and preparation. High mass resolution and accuracy were also demonstrated.
Comments on the Design of the MS-port Meanwhile the peptides are eluted from the chromatographic column with an organic:aqueous solvent containing the MALDI matrix, the liquid flows into the MS-port (i.e., the MALDI target area) by centrifugal force. Once a liquid element (droplet) enters this open area (restricted by the walls of the lid and the upper surface of the bottom substrate) the solvent quickly evaporates and peptides and matrix cocrystallizes on the surface. In order to make this process more robust, i.e., to stronger retain the liquid element while spinning is performed, a hydrophobic pattern was created surrounding the MS-port (then considered a more hydrophilic area). This process of hydrophobic patterning and its flow restriction effect is similar to the process and effect of creating hydrophobic breaks, the difference here being that the hydrophobic pattern surrounding the MS-port is created after the lid has been laminated onto the CD and after the application of the conductive layer. This hydrophobic area has a U-shape (horseshoe) configuration and covers part of the MS-port and part of the lid surface and its wall. Since the liquid element is repelled from this hydrophobic area the droplet preferably stays on the more hydrophilic area during crystallization. In addition to this the crystals are formed on a smaller surface area at some distance away from the walls of the lid. This means that the analyte concentration will be further enhanced (and therefore a higher sensitivity can potentially be reached in the subsequent mass spectrometry analysis) compared to if the crystals were deposited on a larger surface where the sample would more spread out. Also, with automated MALDI analysis it is preferable to have a smaller surface area where the crystals are found as for the laser to more efficiently cover that particular area in a shorter time period (assuming heterogeneous crystal formation, i.e., no "sweet spot"). Moreover, by having the crystals at some distance away from the lid wall less electric field strength disturbances are expected during MALDI analysis due to a non-homogenous field close to the wall. If so, less mass accuracy and resolution is expected. The same would be true for crystals found at different height levels attached to the wall of the lid, i.e., less mass accuracy and resolution would be expected if the crystals were to be irradiated by the laser at different heights along the wall. Finally, any influence of "laser-shadow" by the wall will be diminished.

Certain innovative aspects of the invention is defined in more detail in the appending claims. Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A microfluidic device in the form of a disc comprising an MS-port for presentation of an MS-analyte to an EDI-MS apparatus, said MS-port comprises;

(a) a part of a microchannel structure comprising at least one inlet port, and
    (b) an EDI-area comprising a conductive layer and an EDI-surface from which the MS-analyte is desorbed/ionised, wherein said layer comprises a conductive connection providing voltage and charge transport to the EDI-area or a calibrator area is present in the proximity of said MS-port.

2. The microfluidic device of claim 1, wherein said MS-port comprises a depression in one side of said disc, said depression being in fluid communication with upstream parts of said microchannel structure.

3. The microfluidic device of claim 2, wherein said disc comprises two or more microchannel structures, each of which comprises an MS-port with a depression and an EDI-area comprising a conductive layer and an EDI-surface, the depressions being on the same side of the disc, and the conductive layers of the MS-ports being part of a common conductive layer.

4. The microfluidic device of claim 1, wherein said conductive layer in the MS-port is exposed as an EDI-surface.

5. The microfluidic device of claim 3, wherein the conductive layers of each MS-port is exposed as an EDI-surface, and the common conductive layer extends continuously between the MS-ports and comprises the inner walls of the depressions of the MS-ports.

6. The microfluidic device of claim 1, wherein the MS-port of the microchannel structure is open.

7. The microfluidic device of claim 1, wherein the disc comprises:
   a) an axis of symmetry perpendicular to the disc, and
   b) two or more of said microchannel structures each of which is oriented radially with a liquid flow direction from one of said at least one inlet ports towards the periphery of the disc.

8. The microfluidic device of claim 7, wherein said one inlet port is a sample inlet port.

9. The microfluidic device of claim 7, wherein said MS-ports are at a larger radial distance from the axis of symmetry than said one inlet ports for each of said two or more of said microchannel structure.

10. The microfluidic device of claim 7, wherein said two or more of said microchannel structures each of which is arranged annularly around the axis of symmetry and said MS-ports are at the same radial distance from the axis of symmetry.

11. The microfluidic device of claim 1, wherein said EDI-MS apparatus is a MALDI-MS apparatus.

12. The microfluidic device of claim 1, wherein said EDI-area is a MALDI-area.

13. The microfluidic device of claim 1, wherein said EDI-surface is a MALDI-surface.

14. The microfluidic device of claim 7, wherein each of the MS-ports comprises a depression in one side of the disc, said side being the same for all of the MS-ports.

15. The microfluidic device of claim 7, wherein said conductive layers are part of a common continuous conductive layer.

16. The microfluidic device of claim 7, wherein the conductive layer of each MS-port is exposed as an EDI-surface.

17. The microfluidic device of claim 7, wherein each MS-port comprises a depression with inner walls, and the conductive layers of the MS-port is exposed as EDI-surfaces and are part of a common continuous conductive layer extending continuously between the MS-ports and comprises the inner walls of the depressions of the MS-ports.

18. A microfluidic device in the form of a disc comprising an MS-port for presentation of an MS-analyte to an EDI-MS apparatus, said MS-port comprises:
   (a) a part of a microchannel structure comprising at least one inlet port, and
   (b) an EDI-area comprising a conductive layer and an EDI-surface from which the MS-analyte is desorbed/ionised, wherein said layer comprises a conductive connection providing voltage and charge transport to the EDI-area and a calibrator area is present in the proximity of said MS-port.

19. The microfluidic device of claim 1, wherein said conductive layer of the EDI-area comprises a conducting metal oxide.

20. The microfluidic device of claim 1, wherein said conductive layer of the EDI-area comprises indium tin oxide.

* * * * *